United States Patent
Bridges et al.

(10) Patent No.: US 8,556,842 B2
(45) Date of Patent: Oct. 15, 2013

(54) PERFUSION CIRCUIT AND USE THEREIN IN TARGETED DELIVERY OF MACROMOLECULES

(75) Inventors: Charles R. Bridges, Charlotte, NC (US); Hansell H. Stedman, Norristown, PA (US); Charles Yarnall, Lafayette Hill, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 27 days.

(21) Appl. No.: 13/294,290

(22) Filed: Nov. 11, 2011

(65) Prior Publication Data
US 2012/0053502 A1 Mar. 1, 2012

Related U.S. Application Data

(63) Continuation of application No. 11/664,245, filed as application No. PCT/US2005/034283 on Sep. 26, 2005, now abandoned.

(60) Provisional application No. 60/704,956, filed on Aug. 3, 2005, provisional application No. 60/614,892, filed on Sep. 30, 2004.

(51) Int. Cl.
| | | |
|---|---|---|
| *A61M 37/00* | (2006.01) | |
| *A61M 29/00* | (2006.01) | |
| *A61M 31/00* | (2006.01) | |
| *A61N 1/30* | (2006.01) | |

(52) U.S. Cl.
USPC .......... 604/4.01; 604/21; 604/509; 604/96.01

(58) Field of Classification Search
USPC ......... 604/4.01, 6.09, 6.11, 6.13, 6.14, 96.01, 604/103.07, 19, 21, 509
See application file for complete search history.

(56) References Cited

U.S. PATENT DOCUMENTS

| | | |
|---|---|---|
| 5,069,662 A | 12/1991 | Bodden |
| 5,320,605 A | 6/1994 | Sahota |
| 5,451,207 A | 9/1995 | Yock |
| 5,728,066 A | 3/1998 | Daneshvar |
| 5,813,842 A | 9/1998 | Tamari |
| 6,071,258 A | 6/2000 | Dalke et al. |
| 6,177,403 B1 | 1/2001 | Stedman |
| 6,267,747 B1 | 7/2001 | Samson et al. |

(Continued)

FOREIGN PATENT DOCUMENTS

| | | |
|---|---|---|
| WO | WO 98/10088 A1 | 3/1998 |
| WO | WO 99/31982 A1 | 7/1999 |

(Continued)

OTHER PUBLICATIONS

Boshart, et al., A Very Strong Enhancer is Located Upstream of an Immediate Early Gene of Human Cytomegalovirus, Cell, vol. 41, pp. 521-530, (Jun. 1985).

(Continued)

*Primary Examiner* — Leslie Deak
(74) *Attorney, Agent, or Firm* — Howson & Howson LLP

(57) ABSTRACT

A perfusion circuit and a use thereof for delivering a substance to a subject's heart in situ during cardiopulmonary bypass surgery are provided. The perfusion circuit defines a path for re-circulating a solution containing a macromolecular complex through a coronary circulation circuit through a subject's heart during a surgical procedure in which the substance is prevented from being delivered to the subject's other organs.

20 Claims, 5 Drawing Sheets

(56) References Cited

U.S. PATENT DOCUMENTS

| | | |
|---|---|---|
| 6,508,777 B1 | 1/2003 | Macoviak et al. |
| 6,537,241 B1 | 3/2003 | Odland |
| 6,673,039 B1 | 1/2004 | Stedman et al. |
| 6,699,231 B1 | 3/2004 | Sterman et al. |
| 6,726,651 B1 | 4/2004 | Robinson et al. |
| 6,776,771 B2 | 8/2004 | van Moorlegen et al. |
| 7,214,369 B2 | 5/2007 | Wolff et al. |
| 7,722,596 B2 | 5/2010 | Shapland et al. |
| 2002/0107504 A1 | 8/2002 | Gordon |
| 2003/0040665 A1 | 2/2003 | Khuri |
| 2003/0216332 A1 | 11/2003 | Chamberlain et al. |
| 2004/0126879 A1 | 7/2004 | Schneider et al. |
| 2006/0116627 A1 | 6/2006 | Bridges et al. |
| 2006/0258980 A1 | 11/2006 | Bridges et al. |
| 2007/0073264 A1 | 3/2007 | Stedman et al. |
| 2009/0054823 A1 | 2/2009 | Bridges et al. |
| 2009/0287185 A1 | 11/2009 | Bridges |
| 2011/0112510 A1 | 5/2011 | Stedman et al. |

FOREIGN PATENT DOCUMENTS

| | | |
|---|---|---|
| WO | WO 99/43360 A1 | 9/1999 |
| WO | WO 99/59666 A1 | 11/1999 |
| WO | WO 2005/027995 A2 | 3/2005 |
| WO | WO 2005/030292 A2 | 4/2005 |

OTHER PUBLICATIONS

Bridges, et al., Global Cardiac-Specific Transgene Expression Using Cardiopulmonary Bypass with Cardiac Isolation, Ann. Thorac. Surg., 73:1939-46, (Jun. 2002).

Gossen, et al., Transcriptional Activation by Tetracyclines in Mammalian Cells, Science, vol. 268, No. 5218, pp. 1766-1769, (Jun. 23, 1995).

Greelish, et al., Stable Restoration of the Sarcoglycan Complex in Dystrophic Muscle Perfused with Histamine and a Recombinant Adeno-Associated Viral Vector, Nature Medicine, 5(4):439-443 (Apr. 1999).

Harvey, et al., Inducible Control of Gene Expression: Prospects for Gene Therapy, Curr. Opin. Chem. Biol., 2:512-518, (Aug. 1998).

Koenig, et al., The Complete Sequence of Dystrophin Predicts a Rod-Shaped Cytoskeletal Protein, Cell, vol. 53, pp. 219-228, (Apr. 22, 1988).

Li, et al., Synthetic Muscle Promoters: Activities Exceeding Naturally Occurring Regulatory Sequences, Nature Biotechnology, vol. 17, pp. 241-245, (Mar. 1999).

Magari, et al., Pharmacologic Control of a Humanized Gene Therapy System Implanted into Nude Mice, J. Clin. Invest., vol. 100, No. 11, pp. 2865-2872, (Dec. 1997).

No, et al., Ecdysone-Inducible Gene Expression in Mammalian Cells and Transgenic Mice, Proc. Natl. Acad. Sci., vol. 93, pp. 3346-3351, (Apr. 1996).

Ragot, et al., Efficient Adenovirus-Mediated Transfer of a Human Minidystrophin Gene to Skeletal Muscle of mdx Mice, Nature, vol. 361, pp. 647-650, (Feb. 18, 1993).

Sambrook, et al., Functional Components of Mammalian Expression Vectors, Molecular Cloning, pp. 16.5-16.6 (1989).

Stokes, et al., Experimental Maintenance of Life by a Mechanical Heart and Lung During Occlusion of the Venae Cavae Followed by Survival, Surgery, Gynecology and Obstetrics, 91: 138-156 (1950).

Wang, et al., Ligand-Inducible and Liver-Specific Target Gene Expression in Transgenic Mice, Nature Biotechnology, vol. 15, pp. 239-243, vol. 15, (Mar. 1997).

Wang, et al., Positive and Negative Regulation of Gene Expression in Eukaryotic Cells with an Inducible Transcriptional Regulator, Gene Therapy, 4, pp. 432-441, (May 1997).

Yue, et al., Microdystrophin Gene Therapy of Cardiomyopathy Restores Dystrophin-Glycoprotein Complex and Improves Sarcolemma Intergrity in the Mdx Mouse Heart, Circulation, 108:1626-1632, (Sep. 2003).

International Search Report dated Oct. 3, 2006 in the corresponding International Patent No. PCT/US05/34283, published WO 2006/039218 A2.

Jul. 30, 2008 Office Action and Notice of References Cited in U.S. Appl. No. 10/573,129.

Response to Jul. 30, 2008 Office Action in U.S. Appl. No. 10/573,129.

Apr. 7, 2009 Office Action and Notice of References Cited in U.S. Appl. No. 10/573,129.

Response to Apr. 7, 2009 Office Action in U.S. Appl. No. 10/573,129.

Jan. 8, 2010 Office Action in U.S. Appl. No. 10/573,129.

Response to Jan. 8, 2010 Office Action in U.S. Appl. No. 10/573,129.

Aug. 31, 2010 Office Action in U.S. Appl. No. 10/573,129.

Aug. 16, 2010 Office Action and Notice of References Cited in priority U.S. Appl. No. 11/664,245.

Response to Aug. 16, 2010 Office Action and Notice of References Cited in priority U.S. Appl. No. 11/664,245.

Feb. 24, 2011 Office Action and Notice of References Cited in priority U.S. Appl. No. 11/664,245.

Response to Feb. 24, 2011 Office Action and Notice of References Cited in priority U.S. Appl. No. 11/664,245.

Aug. 11, 2011 Office Action and Notice of References Cited in priority U.S. Appl. No. 11/664,245.

Nov. 19, 2010 Office Action in U.S. Appl. No. 12/086,024.

Response to Nov. 19, 2010 Office Action in U.S. Appl. No. 12/086,024.

Apr. 27, 2011 Office Action in U.S. Appl. No. 12/086,024.

Response to Apr. 27, 2011 Office Action in U.S. Appl. No. 12/086,024.

Jan. 5, 2012 Office Action in U.S. Appl. No. 13/008,379.

Fargnoli, et al., A Pharmacokinetic Analysis of Molecular Cardiac Surgery With Recirculation Mediated Delivery of βARKct Gene Therapy: Developing a Quantitative Definition of the Therapeutic Window, J. Card Fail., Aug. 2011, 17(8):691-699.

Katz, et al., Gene therapy during cardiac surgery: role of surgical technique to minimize collateral organ gene expression, Interactive Cardiovascular and Thoracic Surgery, Sep. 2010, 11:727-731.

Su, et al., Uniform Scale-Independent Gene Transfer to Striated Muscle After Transvenular Extravasation of Vector, Circulation Jun. 2005, 112:1780-1780 and 16 pp. Supplement.

PERFUSION CIRCUIT AND USE THEREIN IN TARGETED DELIVERY OF MACROMOLECULES

CROSS-REFERENCE TO RELATED APPLICATIONS

This application is a continuation of U.S. patent application Ser. No. 11/664,245, filed Apr. 4, 2008, which is a national stage application under 35 U.S.C. 371 of PCT/US2005/034283, filed Sep. 26, 2005 (now abandoned), which claims the benefit under 35 U.S.C. 119(e) of the priority of U.S. Patent Application No. 60/704,956 filed Aug. 3, 2005 (now expired) and claims the benefit under 35 U.S.C. 119(e) of the priority of U.S. Patent Application No. 60/614,892 filed Sep. 30, 2004 (now expired), which applications are incorporated by reference herein.

STATEMENT REGARDING FEDERALLY SPONSORED RESEARCH OR DEVELOPMENT

This invention was made with government support under grants NIBIB 1-R21-EB003223-01 and NIBIB 5-R21-EB003223-02 awarded by the National Institutes of Health (NIH). The US government has certain rights in this invention.

BACKGROUND OF THE INVENTION

The present invention relates to a perfusion circuit for use in delivering substances, such as macromolecular complexes, including small molecules, gene therapy vectors, or the like to the heart.

Cardiovascular disease is a leading cause of death in the United States, and heart failure is a major public health problem in the United States. Gene therapy may provide promising new therapies for this vexing public health problem. However, gene delivery is the most important as yet unsolved problem limiting the applicability of gene therapy for the treatment of heart failure. This applies equally to heart failure due to defined X-linked or autosomal recessive gene defects and to the more common forms of heart failure without a well-defined genetic basis since promising vectors and therapeutic transgenes have been identified for both.

Bridges et al., Annals of Thoracic Surgery, 73:1939-1946 (2002) describe a cardiopulmonary surgical technique for a so-called "incomplete isolation" of a subject's heart in situ. The cardiac isolation technique requires the formation of two separate cardiopulmonary bypass circuits, one for systemic circulation of the body and one for antegrade cardiac circulation of a gene delivery vector. The technique enables multiple passes, or recirculation, of a macromolecular complex through a subject's heart during cardiopulmonary bypass surgery.

A technique which isolates the heart to permit systemic delivery of genes is described in U.S. Provisional Application No. 60/506,367 filed on Sep. 26, 2003 and its corresponding International Application, International Publication No. WO 2005/030292 (Apr. 7, 2005). In addition, a balloon catheter useful in retrograde perfusion of the heart with drugs, gene therapy vectors or other solutions via the coronary sinus is described in U.S. Provisional Application No. 60/504,743 filed on Sep. 19, 2003 and its corresponding International Publication No. WO 2005/027995, published Mar. 31, 2005.

There is need for a perfusion circuit and surgical method that is capable of optimizing drug or gene delivery to the heart in situ during cardiac isolation.

SUMMARY OF THE INVENTION

Advantageously, the present invention provides a cardiac surgical procedure that allows for complete surgical isolation of the heart in situ so that efficient myocyte gene delivery or the like can be accomplished. The perfusion circuit includes various components to maximize safety during re-circulation of a macromolecular complex solution through the cardiac circuit of the invention. Priming volume of the circuit is controlled and minimized to maximize macromolecular complex solution concentration within the coronary circulation. The circuit allows for the efficient filtering of particulate debris, removal of air bubbles, and decompression of the left and right ventricles during macromolecular complex re-circulation.

Other aspects and advantages of the invention will be apparent from the following detailed description of the invention.

BRIEF DESCRIPTION OF THE DRAWINGS

The foregoing and other objects, features and advantages of the present invention should become apparent from the following description when taken in conjunction with the accompanying drawings, in which.

DETAILED DESCRIPTION OF THE INVENTION

The present invention provides a circuit and surgical method which provide a significant reduction in circuit volume as compared to the antegrade circuit described in the literature (approximately 80% reduction as compared to the circuit described in Bridges et al, cited above, and incorporated by reference). The invention further provides a significant increase (approximately 400% as compared to Bridges et al, cited above), in the concentration of the circulating macromolecular complex. This increase in concentration is provided by the decrease in circuit volume and the fact that there is no longer dilution of the macromolecular complex solution infused by the systemic circulatory system.

The circuit and method of the invention are useful as an adjunct to valve repair or replacement surgery, coronary artery bypass graft surgery or ventricular assist device (VAD) implantation procedures in selected patients, e.g., patients with heart failure. The circuit and method of the invention are also useful in patients with known X-linked or autosomal recessive cardiomyopathy. The circuit and method of the invention are also useful for delivery of angiogenic macromolecular complexes (e.g., transgenes) to the myocardium to treat coronary ischemia is desirable, particularly in situations where global delivery is desirable. A variety of other applications for the circuit and method of the invention will be readily apparent to one of skill in the art.

As used herein, the term "macromolecular complex" encompasses any biologically useful moiety that can be transferred into the targeted cells (e.g., striated cardiac muscle cells, or other muscle cells or tissues). Examples of suitable macromolecular complexes include vectors composed of nucleic acids, including RNA and DNA molecules, dominant negative mutants, enzymes, proteins, peptides, or non-proteinaceous molecules, which may include small molecules or other chemical moieties.

The circuit and surgical method of the invention are described in detail as follows.

Figure 1:
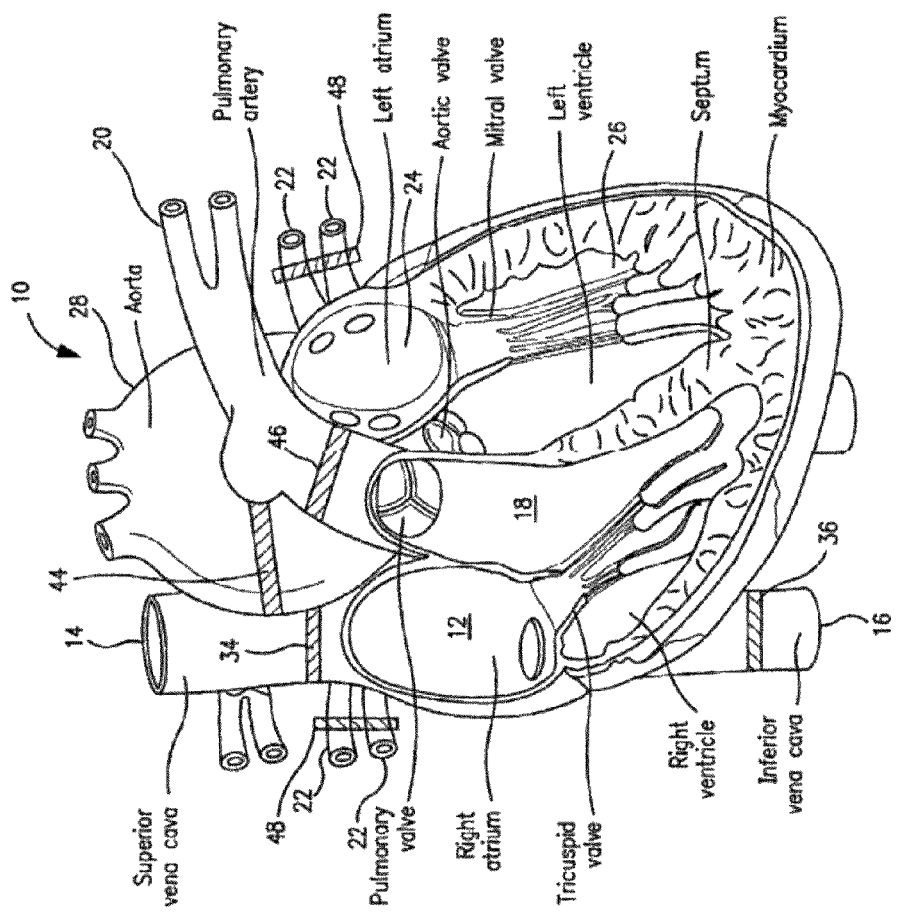
FIG. 1 is a view of a heart.

The basic structure of a human heart 10 is illustrated in FIG. 1. Oxygen-poor blood is returned to the right atrium 12 of the heart via two large veins, the superior vena cava 14 and the inferior vena cava 16, and is pumped into the right ventricle 18 and then to the pulmonary artery 20 before passing to the lungs. Oxygen-rich blood returns from the lungs via four pulmonary veins 22 into the left atrium 24, is pumped into the left ventricle 26, and thereafter, flows into the aorta 28 where it is circulated throughout the body. Coronary arteries (not shown) connect to the aorta 28 and provide oxygen-rich blood to the heart. A network of coronary veins (not shown) returns the oxygen-poor blood utilized by the heart into the right atrium 12 via the coronary sinus (not shown).

Figure 2:
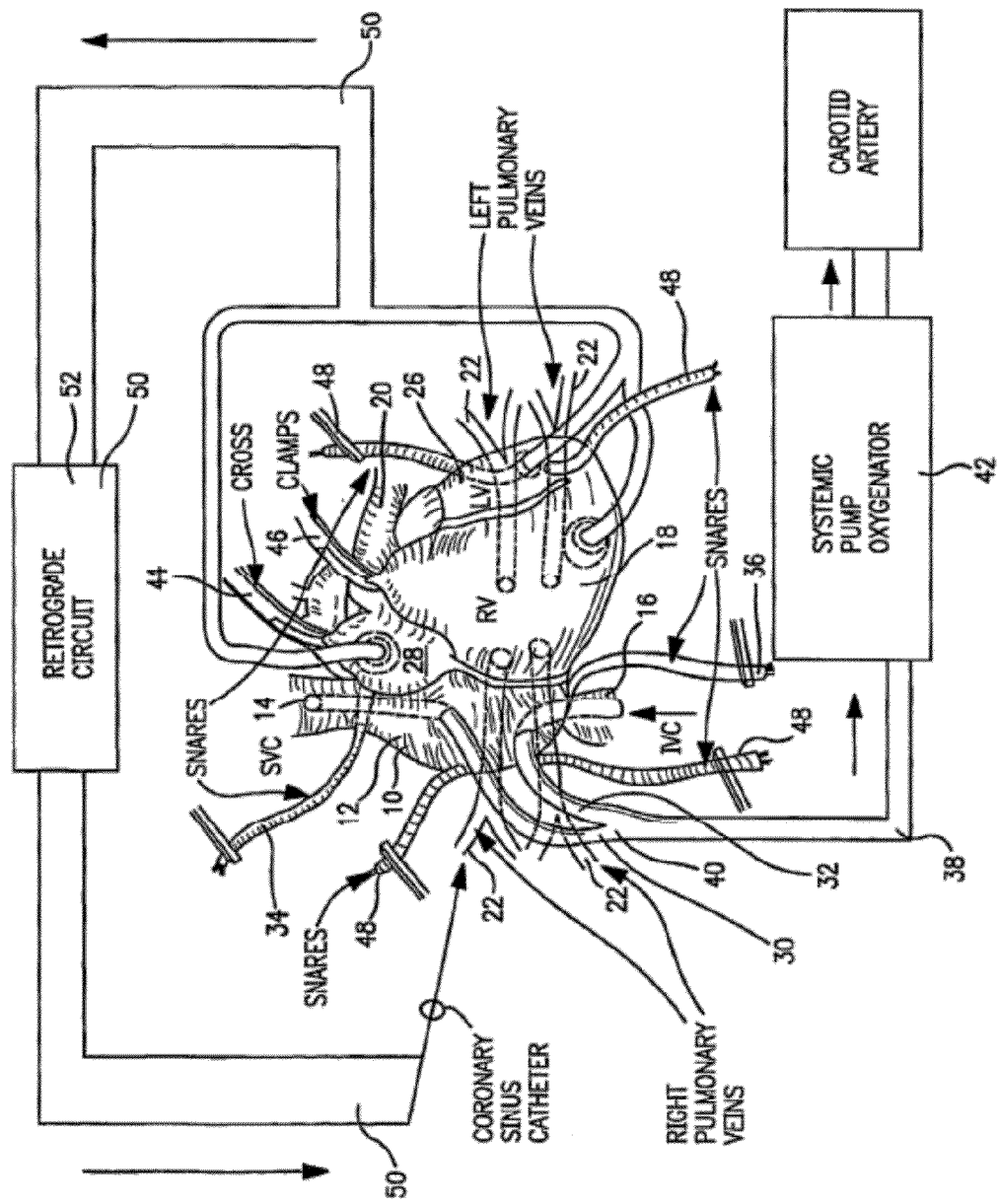
FIG. 2 is a view of a perfusion circuit according to the present invention.

The heart can be isolated in situ via the formation of separate cardiopulmonary bypass circuits for cardiac and systemic circulation. As best illustrated in FIG. 2, right angle venous cannulae, 30 and 32, are positioned within the superior vena cava 14 and the inferior vena cava 16 and snares, 34 and 36, are placed about the superior vena cava 14 and the inferior vena cava 16 so that all systemic venous return flows into a systemic cardiopulmonary bypass circuit 38 via a Y-connector 40. The systemic circuit 38 can include a pump oxygenator 42, or like mechanism, and can return oxygen-rich blood to the subject's femoral and/or carotid arteries via a cannula (not shown). The aorta 28 and pulmonary artery 20 are cross-clamped with clamps 44 and 46 to further isolate cardiac circulation from systemic circulation.

According to the method of the invention, all four pulmonary veins 22 are isolated with snares 48 so that complete two-way isolation is accomplished in that cardiac circulation is isolated from systemic circulation and systemic circulation is isolated from cardiac circulation. This improves delivery of macromolecular complexes to the heart since cardiac circulation is prevented from being diluted with systemic circulation, providing a smaller circuit, and thus, permitting additional re-circulation through the circuit during cardiopulmonary by-pass (CPB).

Figure 3:
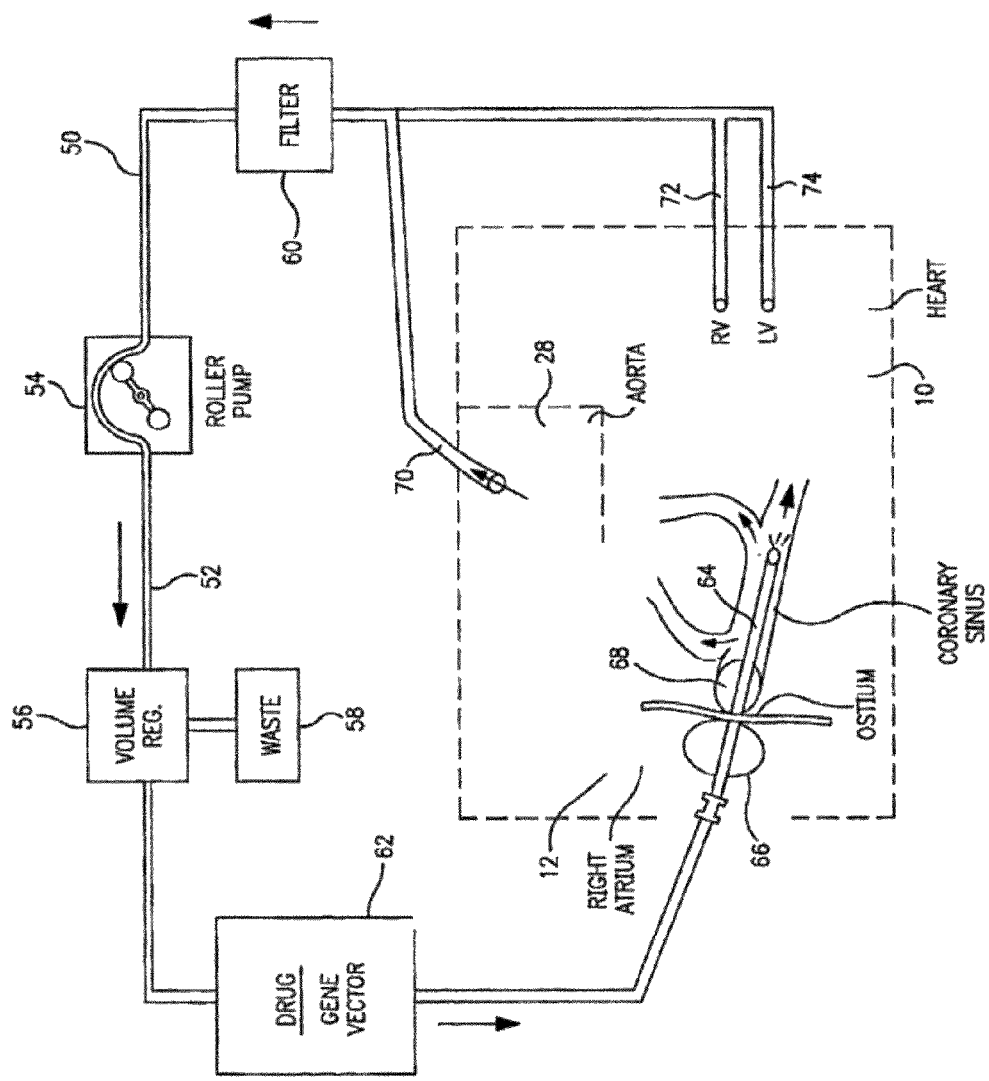
FIG. 3 is a schematic diagram of perfusion circuit according to the present invention.
Figure 4:
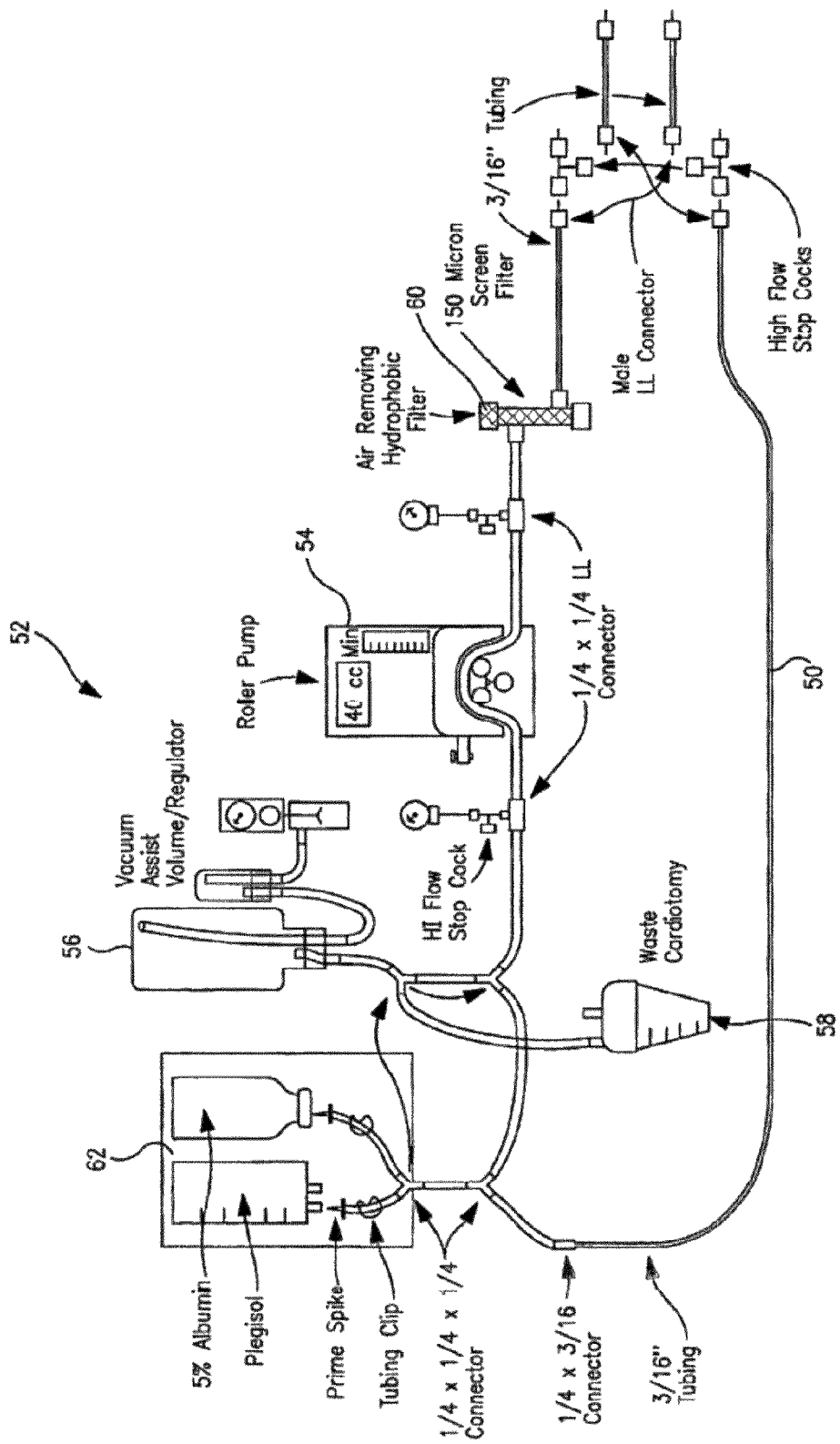
FIG. 4 is a view of an exterior part of the perfusion circuit.

As best illustrated in FIGS. 2 and 3, cardiac circulation follows a path defined by a perfusion circuit 50 which in one embodiment is retrograde. The path provides for retrograde perfusion via the coronary sinus, as illustrated in FIG. 3. Thus, the path permits multi-pass retrograde re-circulation of macromolecular complex solution through the "completely" isolated coronary circulation within the heart. However, another embodiment provides a combination of retrograde and antegrade perfusion; this can be readily accomplished using the circuit of the invention. In yet another embodiment, antegrade perfusion is used.

As illustrated in FIGS. 2 and 3, the heart defines only a portion of the circuit 50. The exterior circuit part 52 includes a number of components that enhance the safety of the cardiac isolation procedure. Preferably, the exterior circuit part 52 includes a pump, such as a roller pump 54, for controlling the rate of circulation of the macromolecular complex solution through the circuit 50. Preferably, a vacuum-assist volume regulator 56, or the like, is utilized to prevent distention of the heart due to volume gaining access to the cardiac circuit from the systemic circuit or elsewhere. Volume regulation is also important to ensure that priming volume is minimized to thereby maximize the concentration of the macromolecular complex being re-circulated through the retrograde coronary circulation path in the heart. A waste cardiotomy 58 can be utilized with regulator 56 to collect waste particulate debris from the circuit. Further, an air-removing hydrophobic filter 60 can be utilized to remove air bubbles from the circuit. In addition, the circuit part 52 includes apparatus 62 for the circulation of a selected drug or other moiety into the cardiac circulation.

In one embodiment, an albumin solution is delivered via this apparatus to the circuit components. This albumin solution, e.g., human serum albumin, can be used as a pre-treating prior to delivery of a macromolecular complex to decrease the likelihood of inactivation of the complex during perfusion. For example, it has previously been demonstrated that adenoviral vector can be inactivated upon contact with the materials which form a perfusion catheter; human serum albumin pre-treatment has been shown to prevent this inactivation. Additionally, other suitable drugs can be delivered via the apparatus 62 including, e.g., Plegisol® cardioplegic solution, or other drugs, gene therapies and/or medication.

In addition, a vascular permeability-enhancing agent can be delivered via this apparatus 62. Although the method of the invention is particularly well suited for delivery of heterologous macromolecular complexes to target cells without utilizing vascular permeability-enhancing agents, because the invention provides total cardiac isolation, it may be desirable or necessary to utilize such agents. Such agents include, e.g., histamine, acetylcholine, an adenosine nucleotide, arachidonic acid, bradykinin, cyanide, endothelin, endotoxin, interleukin-2, ionophore A23187, nitroprusside, a leukotriene, an oxygen radical, phospholipade, platelet activating factor, protamine, serotonin, tumor necrosis factor, vascular endothelial growth factor, a venom, and a vasoactive amine. See, e.g., WO 99/31982, Jul. 1, 1999. Alternatively, if these agents are used, they may be co-infused with the macromolecular complex of the invention as described below.

The term "heterologous" includes, among other things, molecules that are not natively found in combination with the material with which they are being associated. For example, a heterologous molecule is not found in a target cell in the form in which it is delivered to the cell. As another example, heterologous refers to molecules, including nucleic acid sequences, which are derived from the same source but are natively non-contiguous, or molecules that are derived from different sources.

Finally, the exterior circuit part 52 can also include an oxygenator (not shown) and a heat exchanger (not shown) to allow control of the temperature and oxygen content of the solution being circulated through circuit 50.

The above described circuit 50 minimizes circuit volume, or priming volume, and protects the heart from the potentially deleterious effects of over-distention or perfusion of air into the cardiac circulation. In addition, the circuit enables a surgical technique to be utilized that provides high-efficiency, high-concentration delivery of genetic and other materials to the heart.

As stated above, cardiac circulation can be retrograde. In the context of cardiac surgery, retrograde refers to perfusion or infusion in the direction opposite to which blood ordinarily flow, i.e., from the veins to the arteries. Alternatively, cardiac circulation can be simultaneously retrograde, i.e., via the coronary sinus, and antegrade. Antegrade refers to when the flow goes in the direction normal for the cardiac.

According to one embodiment, a dumbbell-shaped balloon retrograde perfusion catheter 64 can form part of the circuit 50. The catheter 64 has a distal end including a pair of asymmetrical-shaped balloons, or balloon sections, 66 and 68, as described in U.S. Provisional Patent No. 60/504,743 filed on Sep. 19, 2003 and in its corresponding International Publication No. WO 2005/027995, published Mar. 31, 2005. The larger balloon, or balloon section, 66 is expanded within the right atrium to a size greater than the ostium and is advanced into engagement with the wall of the right atrium surrounding the ostium. The smaller balloon, or balloon section, 68 is located and expanded within the coronary sinus into engagement with the walls of the coronary sinus adjacent the ostium. Thus, an occlusive plug is formed at the ostium, and the balloons, or balloon sections, sandwich the ostium and anchor the catheter to the coronary sinus. Use of the catheter 64 enables global delivery of the circulating macromolecular complex solution throughout the heart. For instance, improved delivery is provided to the right ventricle at maximal pressure gradient induction since venous "shunting" or "steal" of the solution back into the right atrium is prevented. The pressure gradient and elimination of shunting or steal facilitates and optimizes delivery of macromolecular complex or other compounds globally throughout the heart. This embodiment disallows any cardiac venous effluent that enters the coronary sinus from escaping the retrograde infusion pressure and flow.

The circulating solution exits the heart via a cannula 70 placed within the aorta 28. Cannulae, 72 and 74, placed within the right and left ventricles 18 and 26, respectively, enable decompression of the right and left ventricles during circulation. Thus, the path of the circuit leads back to the exterior part 52 of the circuit 50 where bubbles, waste particulate debris, and excess volume are removed and where temperature and the concentration of drugs, gene vectors or the like is controlled.

Thus, circuit 50 permits safe and effective circulation and recirculation of macromolecular complexes and the like through the heart and the surgical technique minimizes exposure of the macromolecular complexes to other organs within the subject's body.

Transferring a Macromolecular Complex to the Heart of a Subject.

Advantageously, because the heart is completely isolated in situ according to the method of the invention, it permits the infusion or co-infuse of agents which are undesirable for delivery to the systemic circulatory system, including, e.g., endothelial permeabilizing agents or other agents characterized by potentially untoward systemic side effects, thereby limiting delivery to the heart, minimizing the risk of collateral gene expression in other tissues such as the germ line or cornea, and enhancing the therapeutic margin of safety.

Without wishing to be bound by theory, the inventors believe that since the capillaries lie on the venous side of the arteriolar resistor, retrograde (e.g. venous to arterial) vector infusion results in a higher capillary to interstitial pressure gradient favoring filtration of the macromolecular assembly (vector plus transgene). Since the endothelium is rate-limiting for macromolecular molecules (including vector mediated gene transfer), this approach results in enhanced transfection efficiency.

In order to perfuse the heart of a subject according to the present invention, the following general procedure is followed. Typically, the subject is cannulated (e.g., in the left femoral artery) for blood pressure monitoring. The aorta and pulmonary artery are ensnared using umbilical tapes. The pulmonary artery is ensnared by exclusion. The right carotid artery is cannulated. Using previously placed purse strings: 1) a cardioplegia cannula (containing a vent limb) is placed in the ascending aorta; 2) the superior vena cava is cannulated; 3) a retrograde catheter is placed into the coronary sinus and 4) the inferior vena cava is cannulated. The two venous cannulae are connected to a Y connector and connected to the venous limb of the pump circuit. Cardiopulmonary by-pass (CPB) is initiated. All of the pulmonary veins are ensnared, individually or in groups using umbilical tapes and tourniquets. The azygous vein is ligated. The IVC is snared; a cannula is placed into the left ventricular cavity and clamped. A cannula is then placed into the right ventricle and clamped and the purse string is snared. The cardiac circuit, illustrated schematically in FIG. 2, is constructed as described in detail herein. Systemic cooling to, in the range of 15 to 32° C., and preferably, about 30° C. is initiated. The coronary circuit is isolated and the heart emptied of excess volume and air.

Flow into the now isolated cardiac circuit is resumed until the coronary sinus pressure equals between about 50 mm Hg to 100 mm Hg, and preferably, about 60 to 80 mm Hg (typically flow is approximately 100-150 mL/min).

Then a macromolecular complex solution (usually about 0.5 to 3 mL/kg, and preferably about 2.5 mL/kg) is injected slowly into a suitable volume. Suitably, the total volume of the solution infused into the heart is in the range of 20 to 100%, 25 to 90%, 30 to 80%, 40 to 70%, 50 to 60%, of the estimated volume of the heart. For slow injection, infusion is generally over 30 seconds to 1 minute at a circuit flow rate of about 80 cc/min to 140 cc/min, preferably about 100 to 120 cc/min.

In one embodiment, the circulation is stopped and the solution is allowed to dwell for about 30 seconds to ten minutes, or about 1 minute to 9 minutes, or about 2 to 5 minutes. Flow is then restored over one minute to 100 to 120 cc/min, with coronary sinus pressure equal to 60 to 80 mm Hg and the an additional volume of macromolecular complex solution is slowly infused and the solution recirculated. During this interval, the flow is slowly increased to a maximum of 150 cc/min as needed to maintain a coronary sinus pressure of 60 to 80 mm Hg. Suitably, recirculation is for up to 20 minutes where the circulation has been stopped for 10 minutes. Recirculation may be longer where there has been a shorter dwell time. According to the invention, the same macromolecular complex solution or a different macromolecular complex solution can be infused to the heart upon restarting the circulation.

In another embodiment, there is no dwell time, i.e., the circulation is not stopped. In such a circumstance, the solution can be allowed to recirculate for as long as 30 minutes. However, shorter times, e.g., 20 minutes, may be desirable.

The coronary sinus catheter is then removed and the suture tied. The coronary circuit is then flushed, conventional techniques for removing the subject from cardio-pulmonary by-pass are utilized [see, Bridges, et al, cited above] and rewarming is initiated. Where the infusion has been retrograde, the coronary circuit is generally flushed in an antegrade fashion. Typically, this involves infusion of a suitable solution via the aortic route (e.g., the ascending aorta).

In still another aspect, the method of the invention delivers a macromolecular complex of the invention simultaneously in both the retrograde and antegrade direction during complete cardiac isolation.

Suitably, the circuit described herein, optionally utilizing the dual balloon catheter system, can be modified so that rather than infusing solely in a retrograde manner, i.e., into the coronary sinus, infusion is both through the coronary sinus and the aortic route (i.e., antegrade). Outflow is still through the left and right ventricles. In this embodiment, the benefits of elevated venous pressure with more global myocardial delivery are combined.

Macromolecular Complex

A macromolecular complex, as described herein, is selected with a view to the type of therapy or prophylactic use is to be put.

For example, the methods of the invention are useful for treatment of inherited autosomal recessive conditions, such as those associated with the sarcoglycan deficiencies, X-linked cardiomyopathy or the cardiomyopathy associated with Becker's muscular dystrophy. In such an instance, therapy will involve expression of the missing or dysfunctional gene to correct the heart failure phenotype.

Other types of therapies include, e.g., treatment of genetic cardiomyopathies or "idiopathic" heart failure. In addition, the methods and devices of the invention can be used as an adjunct to valve repair or replacement surgery, coronary artery bypass graft surgery or ventricular assist device (VAD) implantation procedures in selected patients with heart failure. Still other therapies include the delivery of angiogenic compounds to the heart (and particularly, the myocardium) to treat coronary ischemia. In another example, compounds useful for cancer therapies, including, e.g., chemotherapeutic agents useful in treatment of cardiac sarcomas and other neoplasms, can be used.

Examples of suitable chemical agents and/or small molecules include, e.g., alkylating agents (i.e., cisplatin, carboplatin, streptazoin, melphalan, chlorambucil, carmustine, methclorethamine, lomustine, bisulfan, thiotepa, ifofamide, or cyclophosphamide); hormonal agents (e.g., estramustine, tamoxifen, toremifene, anastrozole, or letrazole; antibiotics (e.g., plicamycin, bleomycin, mitoxantrone, idarubicin, dactinomycin, mitomycin, or daunorubicin); immunomodulators (e.g., interferons, IL-2, or BCG); antimitotic agents (e.g., vinblastine, vincristine, teniposide, or vinorelbine); tipoisomerase inhibitors (e.g., topotecan, irinotecan, etoposide, or doxorubicin); and other agents (e.g., hydroxyurea, traztuzumab, altretamine, retuximab, paclitaxel, docetaxel, L-asparaginase, or gemtuzumab, ozogamicin).

Still other suitable macromolecular complexes useful in the invention include those molecules carried by vectors. Typically, these vectors carry RNA or DNA molecules, although delivery of moieties other than nucleic acid molecules is encompassed by the present invention. The macromolecular complexes useful in the invention are not limited by size, but rather encompass molecules that, due to their large size, are not able to enter the cell on their own as well as molecules that can infect or transfect cells without the application of the present method.

A. Vectors

A vector includes plasmids, episomes, cosmids, viral vectors, phage, "naked DNA", any of which desirably contains a transgene under the control of regulatory sequences that direct expression thereof in a target cell.

The transgene is a nucleic acid sequence, heterologous to the vector sequences flanking the transgene, which encodes a polypeptide, protein, or other product, of interest. The nucleic acid coding sequence is operatively linked to regulatory components in a manner that permits transgene transcription, translation, and/or expression in a host cell. Suitably, these transgenes may also carry a desired RNA molecule, as described herein.

RNA molecules can include, e.g., tRNA, dsRNA, ribosomal RNA, catalytic RNAs, siRNA, small hairpin RNA, trans-splicing RNA, and antisense RNAs. These RNA molecules can be delivered in the form of a transgene carried by a vector or by other suitable means.

In one embodiment, the macromolecular complex comprises a viral vector. Examples of suitable viral vectors include, without limitation, adenoviruses, picornavirus, adeno-associated viruses, retroviruses, baculoviruses, and lentiviruses, among others. For example, a macromolecular complex can be an adenoviral vector comprising a human minidystrophin gene [Ragot et al, 1993, Nature 361:647-650] or pAdDeltaRSV, which is a modified plasmid containing a full-length dystrophin cDNA [Koening et al, 1998, Cell 53:219-228] with a backbone of a pBSA-2 vector with an RSV promoter operably linked to the dystrophin cDNA, and containing adenoviral 5' and 3' ITRs flanking the promoter-dystrophin cDNA. Currently, adeno-associated viruses (AAV) are considered particularly well suited for delivery to muscle. Typically, a recombinant AAV is composed of, at a minimum, a transgene and its regulatory sequences, and 5' and 3' AAV inverted terminal repeats (ITRs), all packaged in a capsid composed at least in part of proteins encoded by an AAV "cap" gene. In one desirable embodiment, the ITRs of AAV serotype 2 are used. However, ITRs from other suitable serotypes may be selected. However, the invention is not limited to use of viral vectors or, when viral vectors are selected, to use of rAAV.

B. Transgene

When present in a macromolecular complex as defined herein, a transgene is selected with regard to the biological effect desired.

One example of a useful RNA sequence is a sequence which inhibits or extinguishes expression of a targeted nucleic acid sequence in the treated animal. Typically, suitable target sequences include oncologic targets and viral diseases. See, for examples of such targets, the oncologic targets and viruses identified below in the section relating to immunogens.

Another example is for treatment of the symptoms associated with a muscular disorder or cardiomyopathy, one may select from among a number of transgenes associated with muscular dystrophies and/or cardiomyopathies. Examples of suitable genes include, a sarcoglycan protein (e.g., α, β, or δ, or γ), a Muscular Dystrophy protein (dystrophin or utrophin), a minidystrophin or micro dystrophin protein [See, e.g., Y. Yue, et al, Circulation, 108:1623 (September 2003), e-publ. Sep. 2, 2003], calpain, a congenital/limb Girdle Muscular Dystrophy protein (Fukutin, Fukutin-related protein, telethonin, or laminin). Other suitable genes may include beta adrenergic receptor kinase 1 (bARK1), beta andrenoreceptor kinase c-terminase (βARKct), and inhibitors of binding between cardiac myocyte adrenergic receptors and a protein of the Gq subclass. Still other genes include, e.g., carnitine palmityl transferase (CPT) 1 and CTP2, which is implicated in CPT deficiency; dysferlin, which is implicated in limb-girdle MD type 2B and Miyoshi myopathy; thymidine phosphorylase; SMN2 (SMNC), which is implicated in spinal muscular atrophy; and insulin-like growth factor (e.g., Igf1), among others. Still other genes include the sarcoplasmic reticulum $Ca^{2+}$ ATPase (SERCA), SERCA2a, and phospholambin, which are implicated in cardiomyopathies. Other suitable genes include histone deacetylases (HDACs), periostin gene, B-type natriuretic peptide (BNP), pseudophorphorylated mutant of phospholamban (S16EPLN), and Poly-ADP ribose polymerase-1 (PARP-1).

In another embodiment, a transgene may be selected from among transgenes for which expression from a target cell is desired. Such products include those used for treatment of hemophilia, including hemophilia B (including Factor IX) and hemophilia A (including Factor VIII and its variants, such as the light chain and heavy chain of the heterodimer and the B-deleted domain; U.S. Pat. Nos. 6,200,560 and 6,221,349).

Examples of other transgene products include myostatin inhibitors, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), platelet derived growth factor (PDGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), platelet-derived growth factor (PDGF), insulin growth factors I and II (IGF-I and IGF-II), any one of the transforming growth factor α superfamily, including TGFα, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Still other useful transgenes include, e.g., upregulated genes in coronary artery bypass grafting, cardiopulmonary bypass/cardioplegic arrest (CPB/C), including FOS, CYR 61, and IL-6, NR4A1, DUSP1, SLC2A3; genes showing marked upregulation in diabetes mellitus subjects, including MYC, IL8, IL-1beta, amphiregulin, PPP1R3c; MMP (matrix metalloproteinases), Bc1-2, Folbp1, A63V, K70T, E180G alpha-tropomysin (Tm) mutations, FXR (farnesoid X receptor/bile acid receptor), PKC-alpha and others in protein kinase C (PKC) family of serine/threonine hinases, parvalbumin (Parv), Gem, Adenylyl cyclase type VI (AC(VI)), human fibroblast growth factor 4 (Ad5FGF4)—adenoviral vector encoding HFGF4), cardiotrophin-1 (CT-1), Hsp90, troponin I and its isoforms, mutants, and chimeras, angiotensin II Type 2 Receptor (AT2R), S100A1, and human heme oxygenase-1.

Other suitable proteins as for delivery by the method of the invention will be readily apparent. Similarly, transgenes encoding proteins that are expressed on the cell surface of the targeted cells can be delivered by the method of the invention.

C. Regulatory Sequences and Construction of Macromolecular Complexes

Suitably, macromolecular complexes carrying transgenes further contain regulatory sequences operably linked to the encoded gene product. In addition to the major elements identified above, the macromolecular complex (e.g., a vector) also includes conventional control elements that are operably linked to the transgene in a manner that permits its transcription, translation and/or expression in a cell transfected with the macromolecular complex.

As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters that are native, constitutive, inducible and/or tissue-specific, are known in the art and may be utilized.

In one embodiment, the regulatory sequences are optimized for expression in the muscle and/or comprise tissue-specific promoters. For instance, if expression in skeletal muscle is desired, a promoter active in muscle can be used. These include the promoters from genes encoding skeletal β-actin, myosin light chain 2A, dystrophin, muscle creatine kinase, as well as synthetic muscle promoters with activities higher than naturally-occurring promoters (see Li et al., *Nat. Biotech.*, 17:241-245 (1999)). However, one of skill in the art can readily select a suitable constitutive, inducible, or regulated promoter.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell*, 41:521-530 (1985)], the SV40 promoter, the dihydrofolate reductase promoter, the β-actin promoter, the phosphoglycerol kinase (PGK) promoter, and the EF1 promoter [Invitrogen]. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system [WO 98/10088]; the ecdysone insect promoter [No et al, *Proc. Natl. Acad. Sci. USA*, 93:3346-3351 (1996)], the tetracycline-repressible system [Gossen et al, *Proc. Natl. Acad. Sci. USA*, 89:5547-5551 (1992)], the tetracycline-inducible system [Gossen et al, *Science*, 268:1766-1769 (1995), see also Harvey et al, *Curr. Opin. Chem. Biol.*, 2:512-518 (1998)], the RU486-inducible system [Wang et al, *Nat. Biotech.*, 15:239-243 (1997) and Wang et al, *Gene Ther.*, 4:432-441 (1997)] and the rapamycin-inducible system [Magari et al, *J. Clin. Invest.*, 100:2865-2872 (1997)]. Other types of inducible promoters that may be useful in this context are those that are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Methods for assembling and producing a variety of different macromolecular complexes as defined herein are known to those of skill in the art and have been described in textbooks and in the literature. See, e.g., Sambrook et al, Molecular cloning: A Laboratory Manual, Cold Spring Harbor Press, Cold Spring Harbor, N.Y. (1989).

Selection and production of the macromolecular complex is not a limitation of the present invention.

For use in the present invention, a selected macromolecular complex is infused in a physiologically compatible solution. In one embodiment, the solution contains physiologic solution that may be readily selected from among saline, isotonic dextrose, or a glycerol solution, among others that will be apparent to one of skill in the art given the information provided herein. The physiologic solution may be oxygenated; however, the invention is not so limited.

The concentration of a macromolecular complex in the solution can vary depending upon the type of complex selected. Further, a macromolecular complex solution may contain more than one macromolecular complex, e.g., two vectors, a vector and a protein, enzyme, or other moiety, or two or more proteins, enzymes, or other moieties. However, given the information provided in the present invention, one of skill in the art can readily select higher or lower volumes.

Thus, the present invention provides an improved method for delivery of macromolecular complexes to the heart tissue. As described, the use of retrograde perfusion and a smaller circuit without dilution from the systemic circulatory system permits high levels of transfer into the venous interstitium, thereby enhancing transfer into the cardiac muscle as compared to methods known in the art and avoiding transfer of the heterologous molecule to the remainder of the subject.

Clinical Kit

In one aspect, the invention provides a kit for use by a clinician or other personnel. Typically, such a kit will contain a balloon catheter useful in the invention and, optionally, instructions for performing a method as described herein. In another embodiment, the kit will contain a macromolecular complex in a physiologically compatible saline solution and, optionally, instructions for dilution, and performing a method as described herein.

The kit of the invention may also contain an oxygen-transporting agent and/or at least one disposable element of an extracorporeal circulatory support and oxygenation system. For example, at least one disposable element can be an oxygenator having a hollow body, a liquid inlet in fluid communication with the interior of the body, a liquid outlet in fluid communication with the interior of the body, a gas inlet for providing gas to the interior of a gas chamber, at least one gas-permeable membrane separating the gas chamber from the interior of the body, and a gas outlet for permitting gas to exit from the gas chamber, whereby gas exchange is enabled between a fluid in the interior of the body and a gas in the gas chamber. The oxygenator may be constructed as described in U.S. Pat. No. 6,177,403, wherein the gas-permeable membrane comprises PTFE tubing extending within at least a portion of the tube, and wherein the gas chamber comprises the interior of the PTFE tubing.

Thus, the kit of the invention may also comprise an oxygen-transporting agent or at least one disposable element of an extracorporeal circulatory support and/or oxygenation system.

A kit that is useful for performing the method of the invention is contemplated which comprises, in addition to the macromolecular complex, balloon catheter and/or elements of the novel perfusion circuit of the invention, at least one disposable element of an extracorporeal circulatory support and oxygenation system. Preferably, such a kit comprises all of the single-use components needed to perform the method of the invention, including a macromolecular complex, an optional vascular permeability-enhancing agent, a fluid delivery instrument such as a syringe or a length of peristaltic pump tubing, and a cannula such as a hollow bore needle adapted to fit a syringe. Such a kit may also contain a pharmaceutically acceptable carrier, a second cannula, an oxygen-transporting agent, a clearance solution which is substantially free of the macromolecular complex, one or more blood vessel occluding devices, such as a clamp, hemostat, or tourniquet, a disposable oxygenator, and the like.

EXAMPLES

In the following experiments, the inventors compare, using quantitative and histochemical methods, the relative transduction efficiency of a novel method and system of the invention (using cardiopulmonary by-pass, two-way cardiac isolation and retrograde infusion) in the experimental group of animals to a control group in which an equal titer of vector and equal dose of endothelial permeabilizing agent are administered retrograde directly via a catheter in the coronary sinus. Although these studies use an open-chest approach, the control group is designed to simulate what could be achieved using a percutaneous catheter-based transvascular vector delivery technique in a large adult mammal.

The following experiments are illustrative of the method of the invention, but do not limit the invention.

Methods:

Both the two experimental groups, (n=6, cardiopulmonary by-pass, "CPB") and (n=1, "PILOT AAV"); and the control group, (n=3, "CATHETER") consist of normal male canines, each weighing approximately 20 kg. Animals in the CPB group undergo gene delivery using a novel cardiac isolation procedure with retrograde infusion and recirculation of vector using CPB described below. Animals in the CATHETER group undergo gene delivery using a catheter introduced into the coronary sinus without CPB and without isolation of the heart. All animals are cared for in a humane fashion and in compliance with the "Principles of Laboratory Animal Care" formulated by the National Society for Medical Research and the "Guide for the Care and Use of Laboratory Animals" prepared by the Institute of Laboratory Animal Research. One hour before surgery, each animal is premedicated with acepromazine (0.1 mg/kg) and glycopyrrolate (0.001 mg/kg). General anesthesia is induced with ketamine (10 mg/kg) and diazepam (0.5 mg/kg) intravenously and maintained using inhaled oxygen and isoflourane (1% to 2%). Cefazolin (25 mg/kg intravenously) is administered prophylactically.

A. CPB Group:

The left femoral artery is cannulated for blood pressure monitoring. A median sternotomy incision is made and the sternum is divided. Excess thymus tissue is excised (if necessary). Amicar, 5 grams is given I.V. All cannulas and stopcocks are pre-flushed with albumin to avoid inactivation of adenovirus [D J Marshall et al, *Molec. Therapy*, 1:423-429 (2000)]. Purse string sutures are placed around the right atrial appendage, on the right atrium adjacent to the atrioventricular groove, and on the right atrium near its junction with the inferior vena cava. A #1 silk heavy suture is doubly placed around the superior vena cava and connected to a tourniquet. Using pericardial pledgets and 4-0 Prolene suture, a horizontal mattress pledgeted suture is placed on the ascending aorta approximately 1 cm. distal to the aortic root. The aorta and pulmonary artery are ensnared using umbilical tapes. The pulmonary artery is ensnared by exclusion. Heparin is given (130 U/kg). The right carotid artery is cannulated using a 12 French cannula. Using the previously placed purse strings: 1) a cardioplegia cannula (containing a vent limb) is placed in the ascending aorta; 2) the superior vena cava is cannulated using a 26 French right angle cannula; 3) a retrograde catheter is placed into the coronary sinus and 4) the inferior vena cava is cannulated using a 26 French right angle cannula. The two venous cannulae are connected to a Y connector and connected to the venous limb of the pump circuit. CPB is initiated. All of the pulmonary veins are ensnared, individually or in groups using umbilical tapes and tourniquets. The azygous vein is ligated. The IVC is snared with a double loop of 0 silk suture. A purse string is placed in the apex of the left ventricle. Volume is left in the heart. A stab is made in the middle of the purse string, and a cannula is placed into the left ventricular cavity and clamped. A pledgeted purse string is placed in the right ventricular out-flow tract. A cannula is then placed into the right ventricle and clamped and the purse string is snared.

The cardiac circuit is constructed. Systemic cooling to 30 degrees centigrade is initiated. Once the heart fibrillates, the aorta is cross-clamped and benadryl 50 mg., methyl prednisolone 100 mg and cimetidine, 300 mg are administered systemically and simultaneously. Plegisol® cardioplegic solution (Abbott Laboratories, Chicago, Ill., pH adjusted with sodium bicarbonate to pH=7.4), 300 ml at 4° C. is administered to arrest the heart. The virus solution is constituted when bypass is initiated and consists of $10^{13}$ particles of Ad.CMV.LacZ along with 5 micrograms of human VEGF121 (Peprotech, Rocky Hill, N.J.) and 10 micrograms of VEGF 165 (Sigma-Aldrich, St. Louis Mo.) in a total of five cc of PBS. The coronary circuit is isolated and the heart emptied of excess volume and air. Flow into the now isolated cardiac circuit is resumed until the coronary sinus pressure equals 60 to 80 mm Hg (typically flow is approximately 100-150 ml/min). Then one half of the virus solution (approximately 2.5 ml) is injected slowly into 50 ml volume (approximately 2.5 ml/kg) (e.g., over 30 seconds at a circuit flow rate of 100 cc/min). Circulation is stopped and the solution is allowed to dwell for ten minutes. Flow is restored over one minute to 100-120 cc/min, with coronary sinus pressure equal to 60 to 80 mm Hg and the remaining 2.5 ml of virus solution is infused, again over 30 seconds and recirculated for another 20 minutes. During this interval the flow is slowly increased to a maximum of 150 cc/min as needed to maintain a coronary sinus pressure of 60 to 80 mm Hg. The coronary sinus catheter is then removed and the suture tied. The coronary circuit is then flushed antegrade with approximately 500 ml of a colloid solution with 100 mg of methyl prednisolone, 50 mg of diphenhydramine 300 mg of cimetidine added. The aortic cross clamp is removed and flow is restored. Rewarming is initiated. The IVC, SVC and pulmonary vein snares are removed. The RV and LV cannulae are converted to systemic vents. The aortic root cannula is removed. Epinephrine is administered at 1 to 2 mcg/min. Lidocaine (50 mg bolus) is administered and an infusion begun at 1 mg/min. An additional dose of 100 mg of methyl prednisolone, 50 mg of diphenhydramine and 300 mg of cimetidine is administered Aminocaproic acid, 5 mg is given IV. After approximately five minutes of systemic venting, the cross-clamp on the pulmonary artery is removed. The aortic cannula is removed. The RV cannula is removed. Once the heart is contracting well, the LV cannula is removed. Bypass is discontinued after 30 minutes of reperfusion. Once hemodynamic stability is achieved and the heparin is reversed, the chest is closed. A schematic drawing of the cardiac isolation procedure appears in FIG. 2.

B. AAV Group

One "pilot AAV" canine underwent the bypass procedure but $1\times10^{14}$ genome copies of AAV 2/1.CMV.LacZ was utilized (in place of adenovirus), dissolved in approximately 8 cc of PBS. The method of gene delivery was otherwise analogous to the CPB group.

C. Catheter Group (Control)

A median sternotomy incision is made and the sternum is divided. A purse string is placed on the right atrium adjacent to the atrioventricular groove. The retrograde catheter is placed into the coronary sinus. As in the bypass group, the virus solution consists of $10^{13}$ particles of Ad.CMV.LacZ along with 5 micrograms of human VEGF 121 and 10 micrograms of human VEGF 165 in five ml of PBS. One half of the solution (2.5 ml) is injected over 30 seconds with care to clear the catheter dead space (2 ml) before starting the 30-second infusion interval. The solution is allowed to dwell for ten minutes. The remaining 2.5 cc of virus solution is infused over 30 seconds (as above) and allowed to dwell for 20 minutes. The retrograde catheter is then removed. The chest is closed.

D. Assessment of Gene Expression

Within approximately four hours after completion of the procedure, the animals were weaned from mechanical ventilation and inotropic support, and all chest tubes were removed. The animals were returned to an oxygen cage overnight and allowed access to food and water. The next morning they were transferred to cages without supplemental oxygen and sacrificed after six days. For animals in the CBP group and CATHETER group, tissues were procured at necropsy on day six and in the PILOT AAV animal on day 14, following euthanasia with an intravenous overdose of sodium pentobarbital. The animal in the PILOT AAV group received cyclosporine, 10 mg/kg po b.i.d., beginning 5 days prior to the procedure and continued until euthanasia. Cryostat sections of the heart, liver, testis, diaphragm and other organs were incubated overnight at room temperature in X-Gal solution. β-galactosidase enzyme activity was quantified using a chemiluminescent reporter assay system (Galacto-Light Plus, Tropix, Inc., Bedford, Mass.). For comparisons of β-galactosidase activities, a two sample Student's t-test was performed between the CATHETER and CPB groups.

Figure 5:
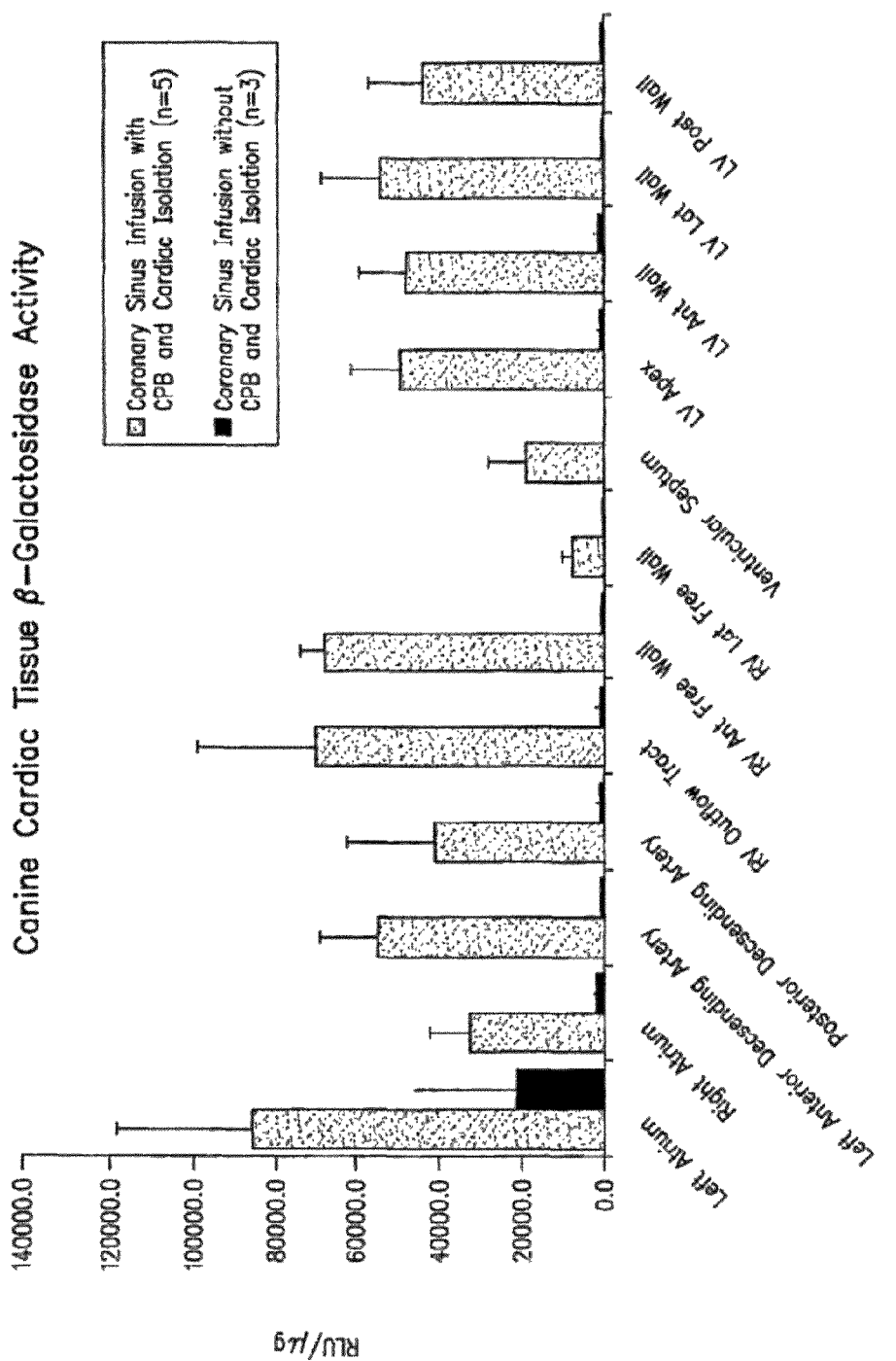
FIG. 5 is a bar chart illustrating expression of a marker gene, β-galactosidase, in cardiac tissue of a canine animal model infused with an exemplary macromolecular complex which delivers the marker gene according to the method of the invention, i.e., with cardiopulmonary by-pass (CPB) and cardiac isolation, as compared to a control group. Expression of the marker gene is shown in relative light units (RLU).

Results:

All animals in the CATHETER group, PILOT AAV group, and five of six animals in the CPB group survived to euthanasia. β-galactosidase activities in the CPB group were several orders of magnitude higher in both the right and left ventricles when compared to the control group (p<0.05, FIG. 5). In contrast, β-galactosidase activities in the CPB group were generally lower in other organs in the CPB group than in the CATHETER group, and in many cases, the differences were statistically significant (p<0.05, FIG. 5). X-gal staining from the CPB group showed unequivocal evidence of myocyte gene expression globally in a significant proportion of cardiac myocytes. No myocyte gene expression was observed in the hearts of the CATHETER group. Whole mount sections stained with X-gal demonstrate transmural Lac Z expression most pronounced in the left ventricle both in the CPB group and in the PILOT AAV animal.

Conclusions:

The present invention permits a higher concentration (100×) of vector to be delivered to the target organ (heart) than would be achieved using a systemic intravenous injection. Even injection into the cardiac arterial or venous system, in the absence of cardiac isolation would result in systemic delivery and lower concentrations of vector delivered to the heart with the potential for collateral gene expression in other organs.

In this study the inventors have shown, for the first time, a convincing and unequivocal demonstration of transgene expression in a significant percentage of cardiac myocytes in the heart of a large adult animal using a transvascular route of delivery with an adenoviral vector.

This study also presents data showing transgene expression in cardiac myocytes in a large region of the left ventricle of a large adult animal using transvascular administration of a rAAV 2/1 vector. Furthermore, the study demonstrates that equivalent results could not be achieved by a simple retrograde catheter infusion technique.

Complete surgical isolation of the heart in situ, using CPB with retrograde coronary sinus infusion and recirculation of vector through the heart results in a several order of magnitude increase in beta-galactosidase activities in the heart, significantly lower betagalactosidase activities in the liver, testis and other organs and no histochemical evidence of transgene expression in the liver. In each of the key comparisons, the differences between the CPB group and the CATHETER group are highly statistically significant. The differences in the histochemical findings are equally striking.

No clinical or histological evidence of significant myocardial toxicity or inflammatory changes were found using this technique.

In an alternative embodiment, the method described above is followed, with the exception that the retrograde catheters described in WO 2005/027995, published Mar. 31, 2005, which allow for global retrograde delivery, are utilized. These catheters are expected to overcome the limitations observed in the prior art catheters utilized in the study described herein, which delivered less macromolecular complex to the right ventricle than was desired.

In yet another embodiment, the method and circuit of the invention are utilized for simultaneous (antegrade/retrograde) cardioplegia delivery in which substantially higher retrograde pressures (up to 80 mm Hg, or higher) may be achieved without apparent myocardial injury.

All documents identified herein are incorporated by reference. While a preferred perfusion circuit and method have been described in detail, various modifications, alterations, and changes may be made without departing from the spirit and scope of the circuit and method according to the present invention as defined in the appended claims. The appended claims are intended to be construed to include all such embodiments and equivalent variations.

The invention claimed is:

1. A method of delivering a macromolecular complex to a subject's heart, said method comprising the steps of:
    (a) forming a cardiac circuit that isolates a subject's cardiac circulation from the subject's systemic circulation; and
    (b) perfusing a first macromolecular complex solution into the cardiac circuit in a retrograde manner, wherein said first macromolecular complex solution comprises a viral vector carrying a target molecule, wherein said viral vector is a recombinant adenoviral (rAd) vector or a recombinant adeno-associated viral (rAAV) vector.

2. The method according to claim 1, wherein said recombinant adeno-associated viral (rAAV) vector comprises an AAV1 capsid.

3. The method according to claim 1, wherein said recombinant adeno-associated viral (rAAV) vector comprises an AAV2 capsid.

4. The method according to claim 1, wherein said recombinant adeno-associated viral (rAAV) vector comprises AAV2 inverted terminal repeat sequences.

5. The method according to claim 1, wherein said recombinant adeno-associated viral (rAAV) vector comprises a serotype 1 capsid and serotype 2 inverted terminal repeat sequences.

6. The method according to claim 1, wherein said first macromolecular complex solution is recirculated in the cardiac circuit for up to 30 minutes.

7. The method according to claim 6, wherein said subject's cardiac circulation is restarted and a second macromolecular complex solution is infused in the circuit for up to 20 minutes.

8. The method according to claim 7, wherein the second macromolecular complex is different from the first macromolecular complex solution.

9. The method according to claim 1, wherein the subject's cardiac circulation is stopped for up to 10 minutes, thereby allowing the macromolecular complex solution to dwell.

10. The method according to claim 9, wherein the subject's cardiac circulation is stopped for up about 5 minutes.

11. The method according to claim 1, wherein retrograde infusion is through the coronary sinus.

12. The method according to claim 1, where said first macromolecular complex is perfused at about 50 mm Hg to 100 mm Hg.

13. The method according to claim 12, where said first macromolecular complex is perfused at about 100 mm Hg.

14. The method according to claim 12, where said first macromolecular complex is perfused at about 60 to 80 mm Hg.

15. The method according to claim 1, wherein said target molecule is a transgene, a chemical moiety, or a DNA molecule which directs the transcription of an mRNA molecule or a RNA silencing molecule.

16. The method according to claim 15, wherein said target molecule is a transgene.

17. The method according to claim 16, wherein said transgene encodes a sarcoglycan protein, dystrophin, utrophin, a minidystrophin protein, a microdystrophin protein, calpain, Fukutin, Fukutin-related protein, telethonin, laminin, beta adrenergic receptor kinase 1 (bARK1), beta andrenoreceptor kinase c-terminase (βARKct), carnitine palmityl transferase (CPT) 1, CTP2, dysferlin, thymidine phosphorylase; SMN2 (SMNC), insulin-like growth factor, sarcoplasmic reticulum $Ca^{2+}$ ATPase (SERCA), SERCA2a, phoshpholambin, histone deacetylases (HDACs), periostin, B-type natriuretic peptide (BNP), pseudophorphorylated mutant of phospholamban (S16EPLN), or PolyADP ribose polymerase-1 (PARP-1).

18. The method according to claim 16, wherein said transgene encodes Factor VIII or Factor IX.

19. The method according to claim 16, wherein said transgene encodes a myostatin inhibitor, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), platelet derived growth factor (PDGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), platelet-derived growth factor (PDGF), insulin growth factors I and II (IGF-I and IGF-II), TGFα, an activin, an inhibin, a bone morphogenic protein (BMP), a heregluin/neuregulin/ARIA/neu differentiation factor (NDF) growth factor, nerve growth factor (NGF), brain-derived neurotrophic factor (BDNF), neurotrophin NT-3, neurotrophin NT-4/5, ciliary neurotrophic factor (CNTF), glial cell line derived neurotrophic factor (GDNF), neurturin, agrin, a semaphorin a collapsin, netrin-1, netrin-2, hepatocyte growth factor (HGF), an ephrin, noggin, sonic hedgehog or tyrosine hydroxylase.

20. The method according to claim 16, wherein said transgene encodes FOS, CYR 61, IL-6, NR4A1, DUSP1, SLC2A3, MYC, IL8, IL-1beta, amphiregulin, PPP1R3C; a matrix metalloproteinase, Bcl-2, Folbpl, A63V, K70T, E180G alpha-tropomysin (Tm) mutations, FXR (farnesoid X receptor/bile acid receptor), a protein kinase C (PKC) serine/threonine kinase, parvalbumin (Parv), Gem, Adenylyl cyclase type VI (AC(VI)), human fibroblast growth factor 4 (Ad5FGF4)-adenoviral vector encoding HFGF4), cardiotrophin-1 (CT-1), Hsp90, troponin I and its isoforms, mutants, and chimeras, angiotensin II Type 2 Receptor (AT2R), S100A1, or human heme oxygenase-1.

* * * * *